(12) United States Patent
Sorrentino et al.

(10) Patent No.: US 9,549,731 B2
(45) Date of Patent: *Jan. 24, 2017

(54) SURGICAL STAPLE

(71) Applicant: Covidien LP, Mansfield, MA (US)

(72) Inventors: Gregory Sorrentino, Wallingford, CT (US); Kenneth H. Whitfield, North Haven, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/992,410

(22) Filed: Jan. 11, 2016

(65) Prior Publication Data

US 2016/0120537 A1  May 5, 2016

Related U.S. Application Data

(62) Division of application No. 12/817,293, filed on Jun. 17, 2010, now Pat. No. 9,265,500.

(60) Provisional application No. 61/235,155, filed on Aug. 19, 2009.

(51) Int. Cl.
    *A61B 17/064* (2006.01)
    *A61B 17/068* (2006.01)
    *A61B 17/10* (2006.01)

(52) U.S. Cl.
    CPC .......... *A61B 17/064* (2013.01); *A61B 17/068* (2013.01); *A61B 17/0644* (2013.01); *A61B 17/105* (2013.01)

(58) Field of Classification Search
    CPC .............. A61B 17/0487; A61B 17/064; A61B 17/0642; A61B 17/0643; A61B 17/0644; A61B 17/068; A61B 17/0682; A61B 17/0684; A61B 17/0686
    See application file for complete search history.

(56) References Cited

U.S. PATENT DOCUMENTS

| | | |
|---|---|---|
| 3,363,628 A | 1/1968 | Wood |
| D221,730 S | 9/1971 | Marietta, Jr. |
| 3,793,696 A | 2/1974 | Barr et al. |
| 4,317,451 A | 3/1982 | Cerwin et al. |
| 4,407,286 A | 10/1983 | Noiles et al. |
| 4,489,875 A | 12/1984 | Crawford et al. |
| 4,607,638 A | 8/1986 | Crainich |
| 4,671,279 A | 6/1987 | Hill |
| 4,787,387 A | 11/1988 | Burbank, III et al. |
| 5,163,598 A | 11/1992 | Peters et al. |
| 5,246,443 A | 9/1993 | Mai |
| 5,282,829 A * | 2/1994 | Hermes ................ A61B 17/064 411/479 |

(Continued)

FOREIGN PATENT DOCUMENTS

| | | |
|---|---|---|
| EP | 1712186 A2 | 10/2006 |
| GB | 2059747 A | 4/1981 |
| WO | 94/20030 A1 | 9/1994 |

OTHER PUBLICATIONS

Extended European Search Report for EP 16 15 8507 dated Jul. 4, 2016.

*Primary Examiner* — Ashley Fishback

(57) ABSTRACT

A surgical staple, comprising a backspan, a first leg member extending from the backspan, a second leg member extending from the backspan, and at least one substantially continuous channel extending along at least one of an inner surface and an outer surface of the first leg member and the second leg member.

13 Claims, 11 Drawing Sheets

(56) References Cited

U.S. PATENT DOCUMENTS

| | | |
|---|---|---|
| 5,304,204 A | 4/1994 | Bregen |
| 5,342,396 A | 8/1994 | Cook |
| 5,445,648 A | 8/1995 | Cook |
| 5,667,527 A | 9/1997 | Cook |
| 5,732,872 A | 3/1998 | Bolduc et al. |
| 5,749,896 A | 5/1998 | Cook |
| 6,083,242 A | 7/2000 | Cook |
| 6,306,150 B1 | 10/2001 | Levinson |
| 7,108,709 B2 | 9/2006 | Cummins |
| 7,438,209 B1 | 10/2008 | Hess et al. |
| 7,926,691 B2 | 4/2011 | Viola et al. |
| 8,393,517 B2 | 3/2013 | Milo |
| 2005/0107807 A1 | 5/2005 | Nakao |
| 2008/0065154 A1 | 3/2008 | Allard et al. |
| 2009/0005809 A1 | 1/2009 | Hess et al. |

* cited by examiner

SURGICAL STAPLE

CROSS-REFERENCE TO RELATED APPLICATIONS

This application is a divisional of U.S. patent application Ser. No. 12/817,293 filed Jun. 17, 2010, which claims benefit of and priority to U.S. Provisional Application No. 61/235,155 filed Aug. 19, 2009, and the disclosures of each of the above-identified applications are hereby incorporated by reference in their entirety.

BACKGROUND

Technical Field

The present disclosure relates to surgical fasteners and, more particularly, to surgical staples for use in surgical staplers having anvil pockets for forming the staples.

Background of Related Art

Surgical stapling instruments have become critical to many life saving surgical procedures. Surgical staples are usually mechanically inserted into tissue with surgical stapling instruments such as those known as anastomosis devices, including gastrointestinal anastomosis devices and transverse anastomosis devices.

In such devices, the staples are loaded in one or more elongated or annular rows into a cartridge. A mechanism for pushing, or driving the stapler is actuated to drive the staples through tissue toward a deforming anvil. At the conclusion of the driving operation, the legs of each staple are conventionally clamped or bent by the anvil to a closed configuration.

One type of conventional staple used with both gastrointestinal anastomosis and transverse anastomosis-type surgical stapling devices is made of stainless steel or titanium. The undeformed staple is generally U-shaped and includes a back span and two leg members depending substantially perpendicularly from the back span. The staple penetrates the tissue from one side to engage an anvil spaced apart and located at an opposing side of the tissue. The staple is bent by having the legs engage and follow an anvil to form a substantially B-shaped closed staple. In this closed configuration, tissue is compressed between the legs and backspan of the staple.

Conventional staples, such as staples having a substantially circular cross-section, require approximately the same amount of force to form the staple into its final shape as is required to twist or malform the staple. Such staples are susceptible to malformation during formation. In order to minimize the risk of staple malformation, it would be desirable to have a staple that requires less amount of force to fire or properly form the staple than the force needed to twist or malform the staple.

SUMMARY

The present application provides in one aspect a surgical staple comprising a backspan, a first leg member extending from the backspan, a second leg member extending from the backspan, and at least one substantially continuous channel extending along at least one of an inner surface and an outer surface of the first leg member and the second leg member. The surgical staple can optionally be formed from a material selected from the group consisting of titanium and stainless steel.

In one embodiment, the at least one substantially continuous channel extends along the inner surface of the first and second leg members and backspan of the surgical staple. In another embodiment, the at least one substantially continuous channel extends along the outer surface of the first and second leg members and backspan of the surgical staple.

In one embodiment, a transverse cross-section of each leg member includes a length and a height, wherein the length is greater than the height.

The present application also provides in another aspect a staple cartridge for use with a surgical staple comprising a plurality of surgical staples in a spaced relation to each other, each of the surgical staples including a backspan, a pair of deformable legs extending from the backspan and configured to come into contact with anvil pockets for formation of the staple, and at least one substantially continuous channel extending along at least one of an inner surface and an outer surface of the deformable legs.

In another aspect, the present application also provides a directionally biased surgical staple comprising a backspan, a first leg member extending from the backspan, a second leg member extending from the backspan, and at least one substantially continuous channel extending along a surface of at least one of the backspan, the first leg member and the second leg member. A transverse cross-section of each leg member includes a length and a height, the length being greater than the height.

DESCRIPTION OF THE DRAWINGS

Embodiments of the presently disclosed surgical staple are disclosed herein with reference to the drawings, wherein.

DETAILED DESCRIPTION OF EMBODIMENTS

Figure 1:
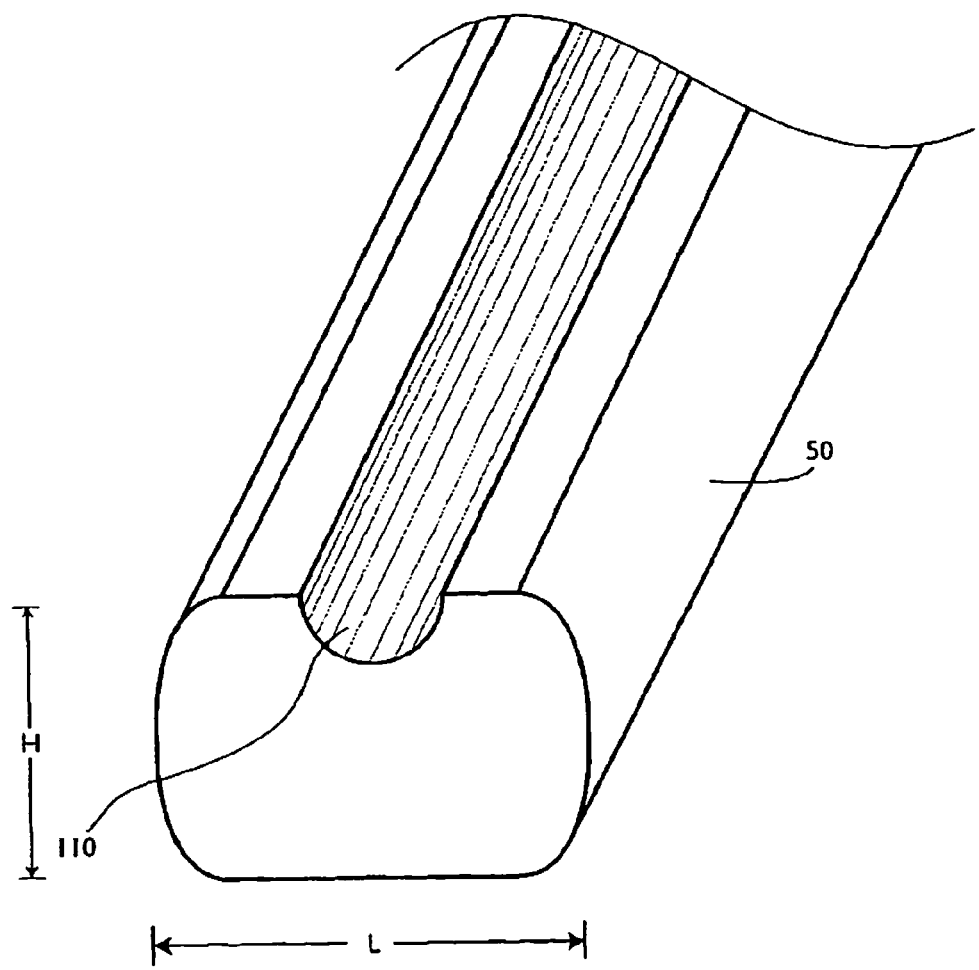
FIG. 1 is a perspective view of a length of stock used to form a staple with an internal channel or an external channel according to embodiments of the present disclosure.

Embodiments of the presently disclosed surgical staple are now described in detail with reference to the drawings, in which like reference numerals designate identical or corresponding elements in each of the several views. As used herein the term "distal" refers to that portion of the surgical staple, or component thereof, farther from the user while the term "proximal" refers to that portion of the surgical staple or component thereof, closer to the user.

Referring initially to FIG. 1, a length of stock 50 is illustrated. Length of stock 50 may be any suitable material used to make surgical staples, such as stainless steel or titanium. It is envisioned that length of stock 50 is cut to an appropriate size and bent into a suitable staple shape, such as the shape shown in FIGS. 2A and 3A for use as a surgical staple e.g., staple 200. Length of stock 50 is shown having a substantially oblate cross-section. A channel 210 is also shown extending continuously along length of stock 50.

Figure 2A:
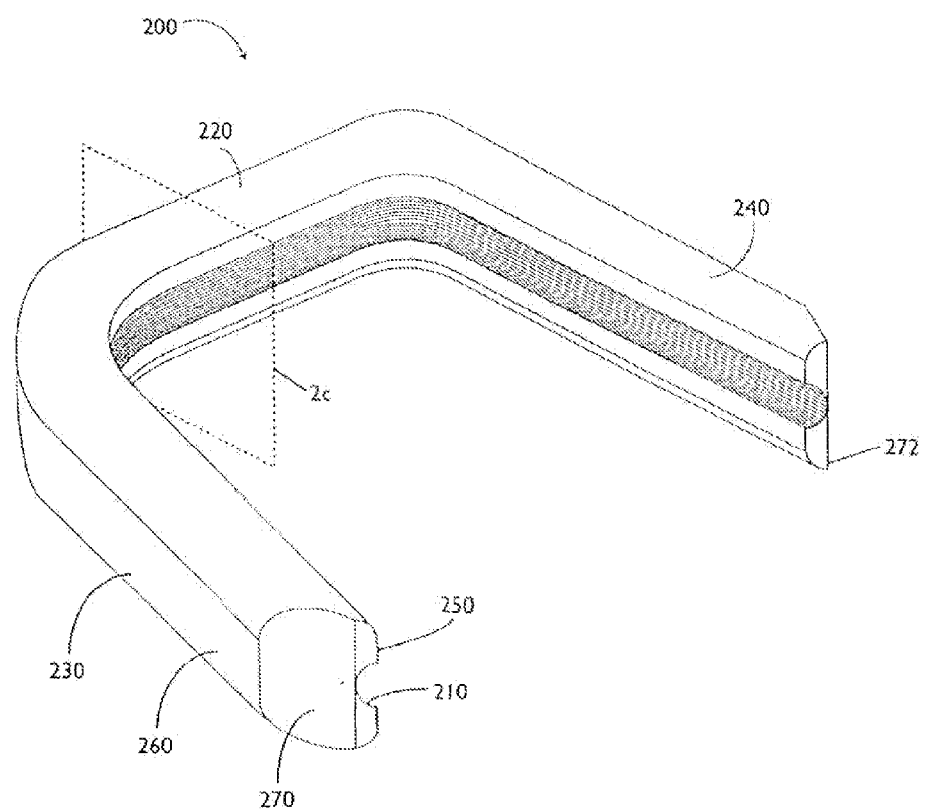
FIG. 2A is a perspective view of an unformed staple using the stock of FIG. 1 having an internal channel.
Figure 2B:
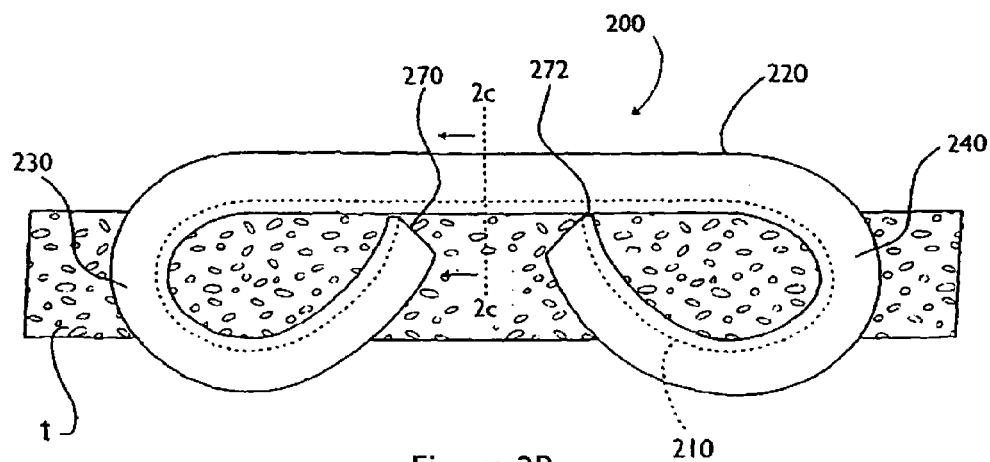
FIG. 2B is a side view of the staple of FIG. 2A illustrating the staple's leg members in a formed configuration through a layer of tissue.
Figure 2C:
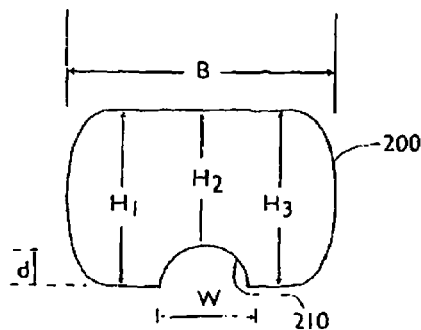
FIG. 2C is a transverse cross-sectional view of the staple of FIGS. 2A and 2B taken along plane 2C in FIG. 2A and along line 2C-2C in FIG. 2B.

A surgical staple, e.g., a directionally biased surgical staple, in accordance with one embodiment of the present disclosure is shown in FIGS. 2A-2C. Specifically, FIGS. 2A-2C refer to surgical staple as reference numeral 200. As can be appreciated with respect to FIG. 1, surgical staples of the present disclosure are made from a length of stock 50. That is, a length of stock 50 may be cut and bent to form a staple-like shape, such as the shape shown in FIG. 2A. Various embodiments of the surgical staple are illustrated in the figures and it is envisioned that the configuration and/or shape of the staple may be varied.

With reference to FIGS. 2A-2C, surgical staple 200 includes a backspan 220, a first leg member 230, a second leg member 240 and a channel 210. First leg member 230 and second leg member 240 each extend from backspan 220, preferably integrally therefrom, and preferably substantially perpendicular thereto, although they alternatively can extend at different angles, e.g. converge or diverge with respect to the backspan. Note the staple legs of the other embodiments herein can also extend substantially perpendicular or at other angles to the backspan and the legs are preferably formed integrally with the backspan. In the illustrated embodiment, channel 210 (e.g., a substantially continuous channel 210) extends along an inner surface 250 of first leg member 230, backspan 220 and second leg member 240. As is discussed in more detail below, inclusion of channel 210 helps facilitate proper firing and/or formation of surgical staple 200 upon contact with an anvil portion such as anvil portion 710 of a surgical stapler 700 (see FIG. 7). Additionally, and as discussed in more detail below, inclusion of channel 210 helps reduce the firing force necessary to properly form the staple and also helps bias staple leg members 230, 240 to form in a certain direction.

With specific reference to FIG. 2B, surgical staple 200 is shown in a deformed orientation (configuration) and through a layer of tissue "t." Specifically, first leg member 230 and second leg member 240 are shown in a deformed condition having a substantially curved shape and surgical staple 200 is shown in a B-like configuration.

Tissue penetrating portions 270 are shown formed adjacent a distal end of leg members 230, 240. Penetrating portions 270 may be of any known configuration that facilitates entry of leg members 230, 240 into tissue "t" to be stapled. Tissue penetrating portions 270 are shown having a chisel-like shape with points 272 adjacent inner facing sides of leg members 230, 240.

Figure 3A:
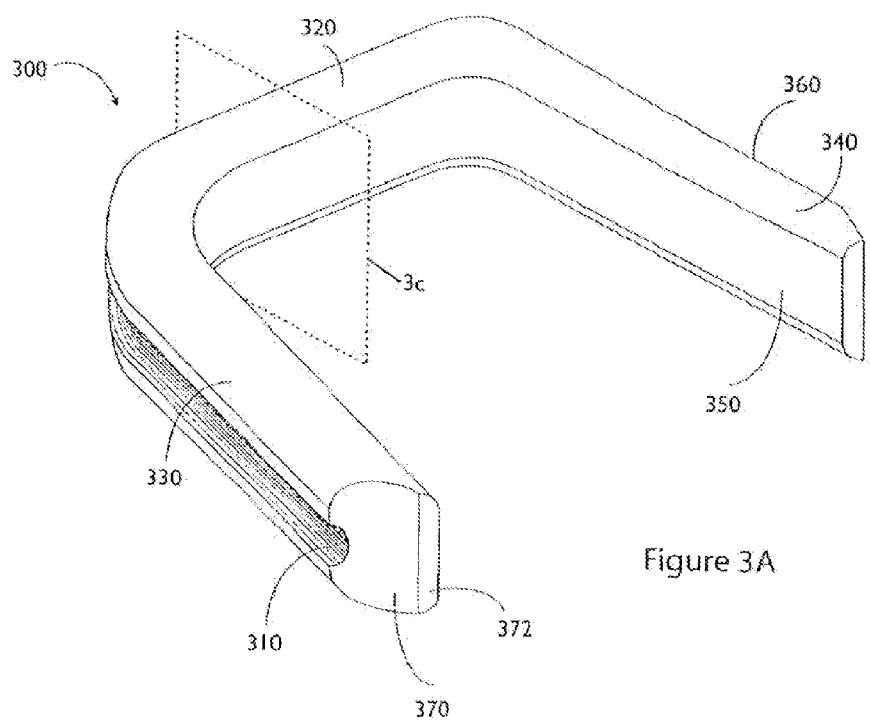
FIG. 3A is a perspective view of an unformed staple of an alternate embodiment using the stock of FIG. 1 having an external channel.
Figure 3B:
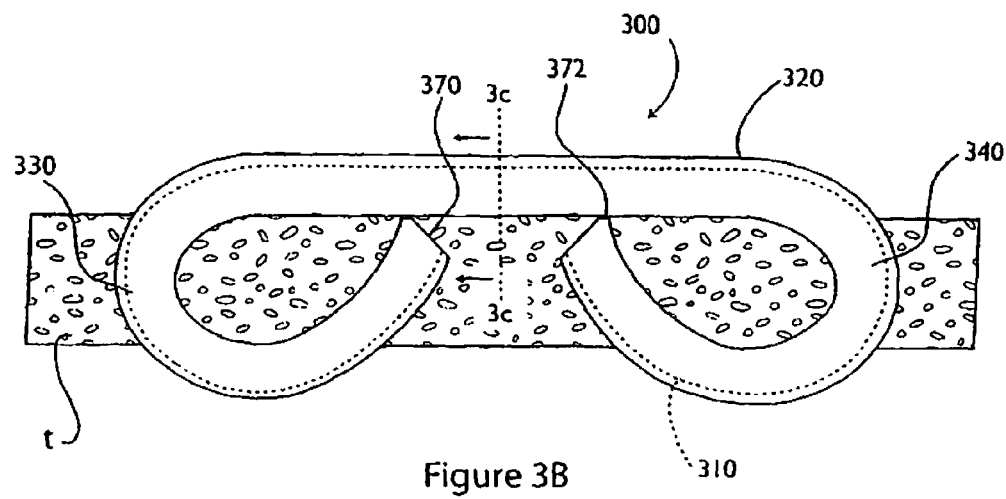
FIG. 3B is a side view of the staple of FIG. 3A illustrating the staple's leg members in a formed configuration and through a layer of tissue.
Figure 3C:
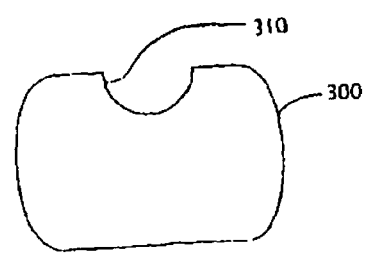
FIG. 3C is a transverse cross-sectional view of the staple of FIGS. 3A and 3B taken along plane 3c in FIG. 3A and along line 3c-3c in FIG. 3B.

With reference to FIGS. 3A-3C, another embodiment of the present disclosure is illustrated. Here, a surgical staple 300 includes a backspan 320, a first leg member 330, a second leg member 340 and a channel 310. First leg member 330 and second leg member 340 each extend from backspan 320, preferably substantially perpendicular thereto. In the illustrated embodiment, channel 310 (e.g., a substantially continuous channel 310) extends along an outer surface 360 of first leg member 330, backspan 320 and second leg member 340. Inclusion of channel 310 helps facilitate proper firing and/or formation of surgical staple 300 upon contact with an anvil portion such as anvil portion 710 of a surgical stapler 700 (see FIG. 7). Additionally, inclusion of channel 310 helps reduce the firing force necessary to properly form a staple and also helps bias staple leg members 330, 340 to form in a certain direction.

With specific reference to FIG. 3B, surgical staple 300 is shown in a deformed orientation (configuration) and through a layer of tissue "t." Specifically, first leg member 330 and second leg member 340 are shown in a deformed condition having a substantially curved shape and surgical staple 300 is shown in a B-like configuration.

Tissue penetrating portions 370 are shown formed adjacent a distal end of leg members 330, 340. Penetrating portions 370 may be of any known configuration that facilitates entry of leg members 330, 340 into tissue "t" to be stapled. Tissue penetrating portions 370 are shown having a chisel-like shape with points 372 adjacent inner facing sides of leg members 330, 340.

As can be appreciated, the transverse cross-sections of surgical staples 200 and 300 are substantially identical (flipped vertically) and may each be formed from length of stock 50 of FIG. 1.

Figure 4A:
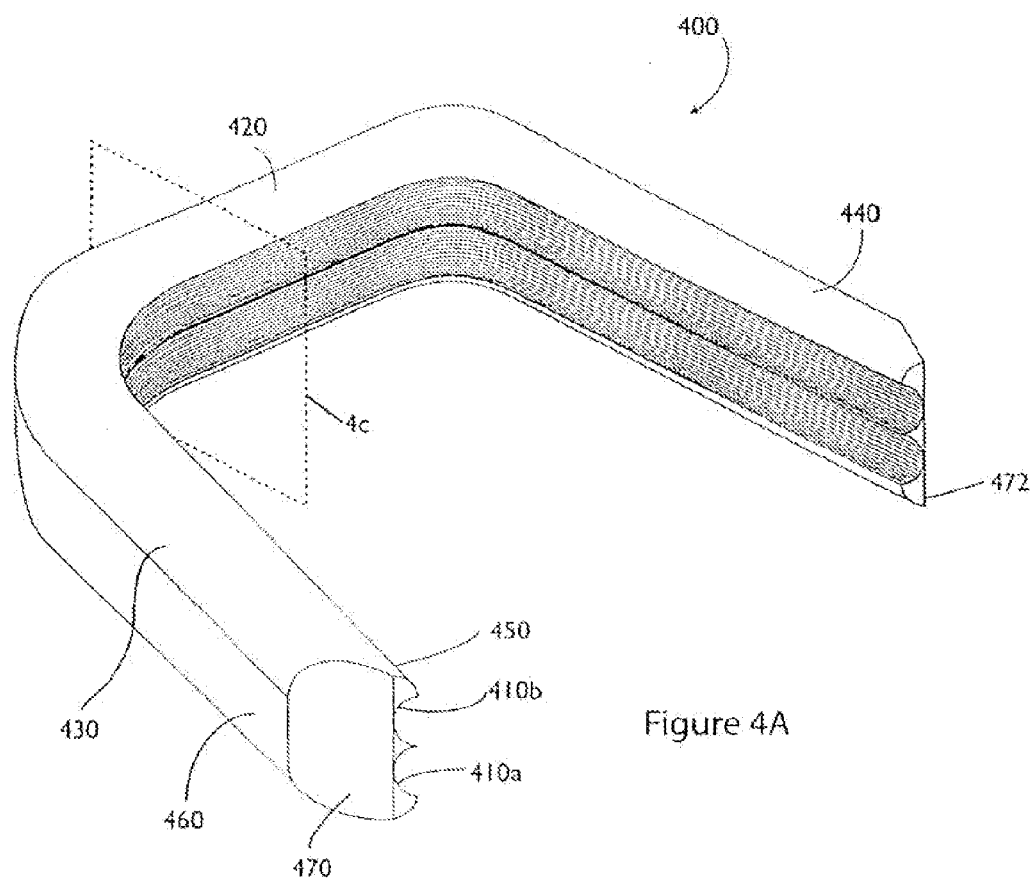
FIG. 4A is a perspective view of an unformed staple having two internal channels in accordance with another embodiment of the present disclosure.
Figure 4B:
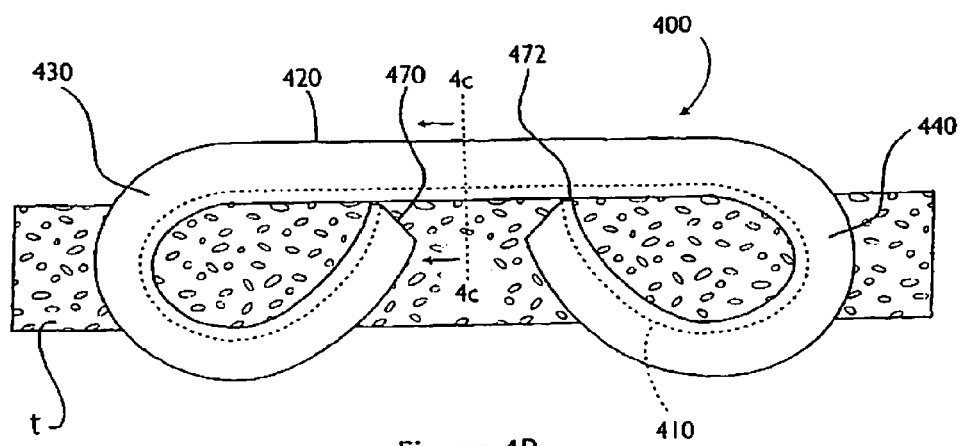
FIG. 4B is a side view of the staple of FIG. 4A illustrating the staple's leg members in a formed configuration through a layer of tissue.

Another embodiment of the present disclosure is illustrated in FIGS. 4A-4B. Here, a surgical staple 400 includes a backspan 420, a first leg member 430, a second leg member 440 and two channels 410a, 410b. First leg member 430 and second leg member 440 each extend from backspan 420. In the illustrated embodiment, channels 410a, 410b (e.g., a substantially continuous channels 410a, 410b) extend along an inner surface 450 of first leg member 430, backspan 420 and second leg member 440. Inclusion of channels 410a, 410b helps facilitate proper firing and/or formation of surgical staple 400 upon contact with an anvil portion such as anvil portion 710 of a surgical stapler 700 (see FIG. 7). Additionally, inclusion of channels 410a, 410b helps reduce the firing force necessary to properly form a staple and also helps bias staple leg members 430, 440 to form in a certain direction.

With specific reference to FIG. 4B, surgical staple 400 is shown in a deformed orientation (configuration) and through a layer of tissue "t." Specifically, first leg member 430 and second leg member 440 are shown in a deformed condition having a substantially curved shape and surgical staple 400 is shown in a B-like configuration.

Tissue penetrating portions 470 are shown formed adjacent a distal end of leg members 430, 440. Penetrating portions 470 may be of any known configuration that facilitates entry of leg members 430, 440 into tissue "t" to be stapled. Tissue penetrating portions 470 are shown having a chisel-like shape with points 472 adjacent inner facing sides of leg members 430, 440.

Figure 5A:
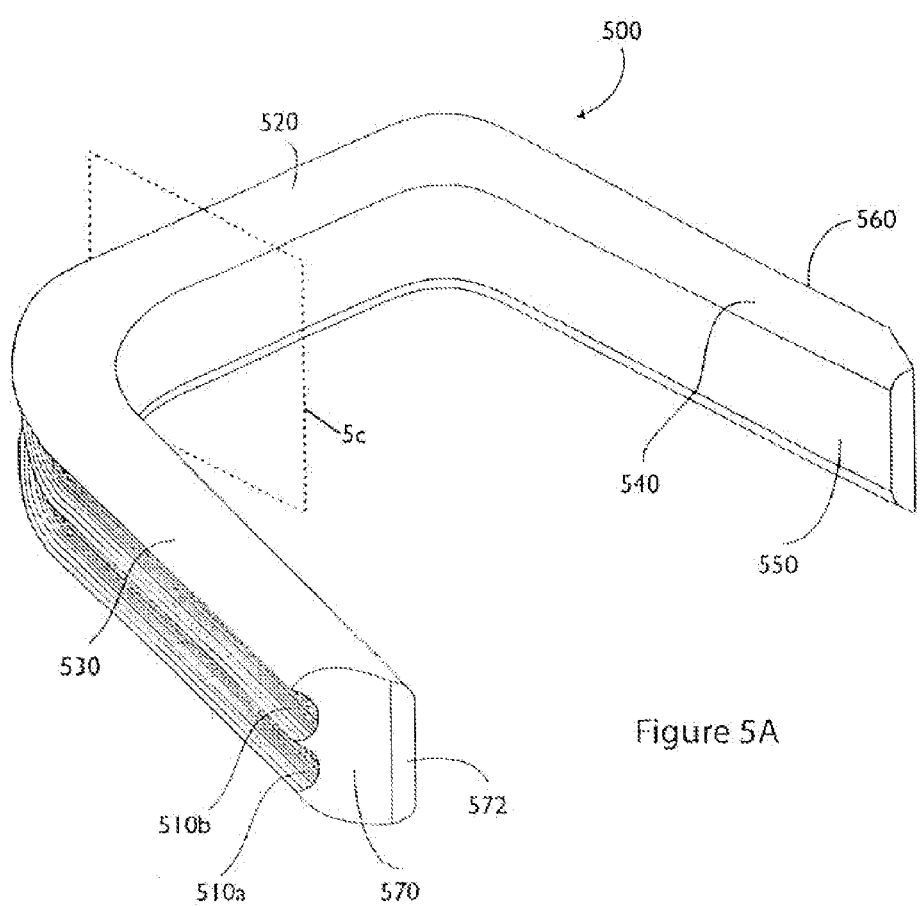
FIG. 5A is a perspective view of an unformed staple having two external channels in accordance with another alternate embodiment of the present disclosure.
Figure 5B:
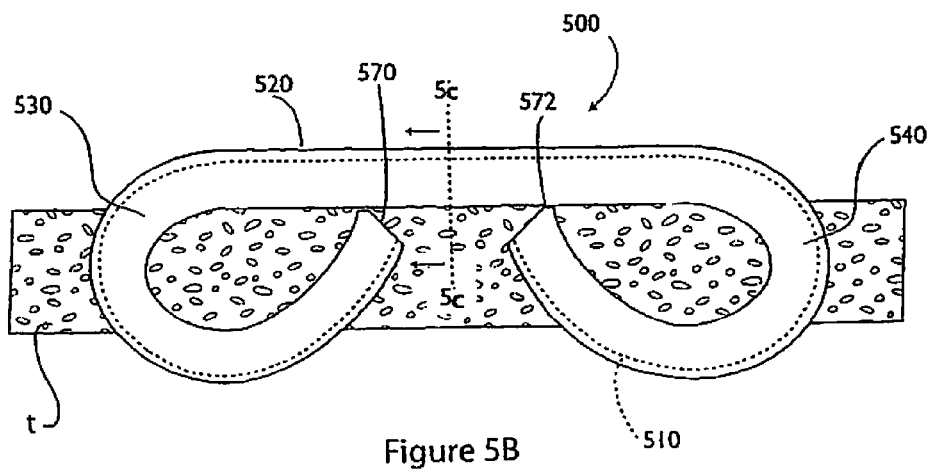
FIG. 5B is a side view of the staple of FIG. 5A illustrating the staple's leg members in a formed configuration and through a layer of tissue.
Figure 5C:
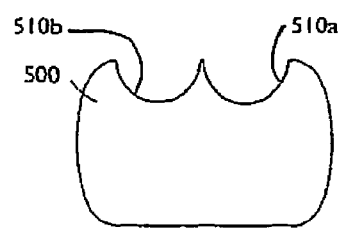
FIG. 5C is a transverse cross-sectional view of the staple of FIGS. 5A and 5B taken along plane 5c in FIG. 5A and along line 5c-5c in FIG. 5B.

Another embodiment of the present disclosure is illustrated in FIGS. 5A-5B. Here, a surgical staple 500 includes a backspan 520, a first leg member 530, a second leg member 540 and two channels 510a, 510b. First leg member 530 and second leg member 540 each extend from backspan 520. In the illustrated embodiment, channels 510a, 510b (e.g., a substantially continuous channels 510a, 510b) extend along an outer surface 560 of first leg member 530, backspan 520 and second leg member 540. Inclusion of channels 510a, 510b helps facilitate proper firing and/or formation of surgical staple 500 upon contact with an anvil portion such as anvil portion 710 of a surgical stapler 700 (see FIG. 7). Additionally, inclusion of channels 510a, 510b helps reduce the firing force necessary to properly form a staple and also helps bias staple leg members 530, 540 to form in a certain direction.

With specific reference to FIG. 5B, surgical staple 500 is shown in a deformed orientation (configuration) and partially through a layer of tissue "t." Specifically, first leg member 530 and second leg member 540 are shown in a deformed condition having a substantially curved shape and surgical staple 500 is shown in a B-like configuration.

Tissue penetrating portions 570 are shown formed adjacent a distal end of leg members 530, 540. Penetrating portions 570 may be of any known configuration that facilitates entry of leg members 530, 540 into tissue "t" to be stapled. Tissue penetrating portions 570 are shown having a chisel-like shape with points 572 adjacent inner facing sides of leg members 330, 340.

As can be appreciated, the transverse cross-sections of surgical staples 400 and 500 are substantially identical (flipped vertically) and may each be formed from the same length of stock (not explicitly illustrated).

Figure 6:
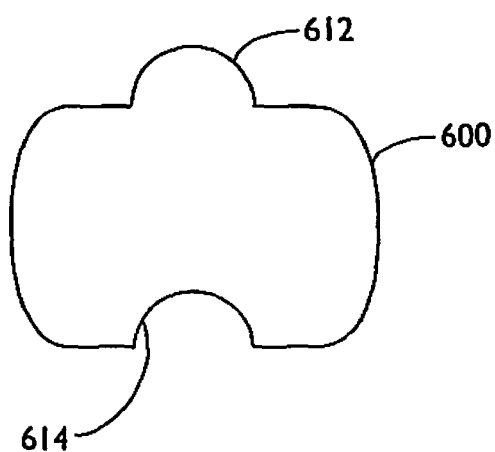
FIG. 6 is a transverse cross-sectional view of a staple having a rib in accordance with an alternate embodiment of the present disclosure.

In the illustrated embodiments, channel e.g., 110 is shown as being semi-circular and concave, however other shapes and orientations of channel 110 are envisioned. Alternatively, and as illustrated by the cross-section in FIG. 6, a rib 612 (e.g., a substantially continuous internal rib or a substantially continuous external rib) or other convexity of surgical staple 600 may be positioned on the opposing side of channel 614. Channel 614 is preferably proportional to or smaller than the dimension of rib 612. Such rib or other convexity can optionally be provided with the staples of the other embodiments disclosed herein.

Further, the size of channel 110 (applicable to the channels of the various staples disclosed herein) is shown as a particular size, but it is contemplated that channel 110 may be of any suitable size. Specifically, it is envisioned that a width "W" of channel 110 (see FIG. 2C) may be between about 0.004 inches and about 0.007 inches and a depth "d" of channel 110 may be between about 0.001 inches and about 0.004 inches. More particularly, width "W" may be between about 0.005 inches and about 0.006 inches and depth "d" may be between about 0.002 inches and about 0.003 inches. Alternatively, the dimensions of channel 110 may be varied accordingly depending on the size and/or configuration of the staple and its intended use.

Additionally, the dimensions of length of stock 50 used to make the various surgical staples disclosed herein are configured to further help bias the staple leg members to form in a certain direction. That is, with reference to surgical staple 200 by way of example, staple 200 includes a length dimension "L" (FIG. 1) greater than its height dimension "H," resulting in a moment of inertia ratio that favors proper formation of surgical staple 200. That is, the force required to properly form the staple is less than the force required to malform or twist the staple. This is applicable to the other staples described herein. More details of such moment of inertia ratios and related calculations are disclosed in U.S. Pat. No. 7,398,907, the entire contents of which are hereby incorporated by reference herein.

The various cross-sectional configurations of the surgical staples illustrated in the figures may be achieved by any suitable method including extrusion, rolling, coining, etc. or any reasonable combination. Particularly, such configurations may be accomplished by flat rolling round wire stock on opposing sides and forming the channel or rib with a mandrel, extruder or form of a predetermined shape and depth. In the fabrication process, stock 50 can be pre-rolled by the wire manufacturer or may be round wire stock which is rolled into the desired cross-sectional configuration by the staple manufacturer.

As mentioned above, the channel(s) of the staples disclosed herein help facilitate proper firing and/or formation of the surgical staple upon contact with the anvil portion such as anvil portion 710 of a surgical stapler 700. The inclusion of the channel affects the cross-sectional area of portions of surgical staple and thus influences various moments of inertia to minimize the likelihood of staple malformation. The cross-sections can be uniform throughout the staple or can vary.

Turning to staples 200 and 300, and with particular reference to staple 200, it being understood that the following is applicable to staple 300, the moment of inertia of cross-section of surgical staple 200 of FIGS. 2A-2C is represented by I, with B representing a base of cross-section and $H_1$, $H_2$, and $H_3$ representing various heights of cross-section (see FIG. 2C).

The moment of inertia, I, of the cross-sectional configuration of the surgical staple 200 illustrated in FIGS. 2A-2C (single notched/channeled staple) is given by the equation:

Moment of Inertia about Forming Axis $$Ixx = \int_{vol} \rho(y^2 + z^2) dV$$

A staple cross-section with a single notch (channel) has by way of example base dimension B=0.01075 in., a first height $H_1$=0.00675 in., a second height $H_2$=0.00425 in., and a third height $H_3$=0.00675 in.

therefore, the Area=$5.609 \times 10^{-0.05}$ in$^2$.

Accordingly, moment of inertia $I_{xx}$=$1.63 \times 10^{-10}$ in$^4$.

Figure 4C:
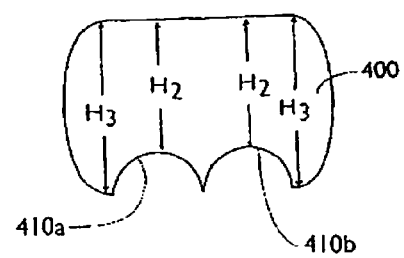
FIG. 4C is a transverse cross-sectional view of the staple of FIGS. 4A and 4B taken along plane 4c in FIG. 4A and along line 4c-4c in FIG. 4B.

The moment of inertia, I, of the cross-sectional configuration of the surgical staple 400 (and staple 500) illustrated in FIGS. 4A-4C (double notched/channeled staple) is given by the equation:

Moment of Inertia about Forming Axis $$Ixx = \int_{vol} \rho(y^2 + z^2) dV$$

A staple cross-section with 2 notches (channels) has by way of example a base dimension B=0.01075 in., and a first and fourth height $H_1$, $H_4$=0.00675 in., and a second and third height $H_2$, $H_3$=0.00425 in.

therefore, the Area=$5.572 \times 10^{-0.05}$

Accordingly, moment of inertia $I_{xx}$=$1.44 \times 10^{-10}$ in$^4$.

The advantage of the channel (notch) can be appreciated by comparing it to the moment of inertia for a directionally biased staple which does not have any channels (notches):

Moment of Inertia About Forming Axis $$Ixx = \int_{vol} \rho(y^2 + z^2) dV$$

A staple cross-section without a notch or rib that has a base dimension B=0.01075 in., and a side height H=0.00675 in.

therefore, the Area=$6.5907 \times 10^{-0.05}$

Accordingly, moment of inertia $I_{xx}$=$2.29 \times 10^{-10}$ in$^4$.

Thus, as can be appreciated, less force is required to form the staple having one channel (notch) compared to the directional staple without any channels.

Since the surgical staple disclosed herein is forced through tissue "t" and the anvil and cartridge, e.g. anvil portion 710 and staple cartridge 720, can flex as tissue is compressed and can move slightly relative to another, the point of contact between staple leg points e.g. leg points 272 of staple 200, and anvil portion 710 may be affected. For example, if anvil portion 710 moves slightly out of alignment, the staple legs will contact a different point of anvil portion 710 which can affect uniform formation of the surgical staple. Additionally, due to manufacturing tolerances, the staple points 272 may not contact the anvil pockets in the exact optimal location. Although such staple formation is clinically satisfactory and effective, the surgical staples of the present disclosure may provide for more uniform formation and may accommodate greater manufacturing tolerances as they are more resistant to twisting. That is, the disclosed surgical staples will have the tendency to bend in the direction of the channel e.g., channel 210, which is desired because, here, the dimension of the surgical staple including the channel defines the desired bending direction. By relaxing manufacturing tolerances, the cost of manufacturing may be reduced as well.

Figure 7:
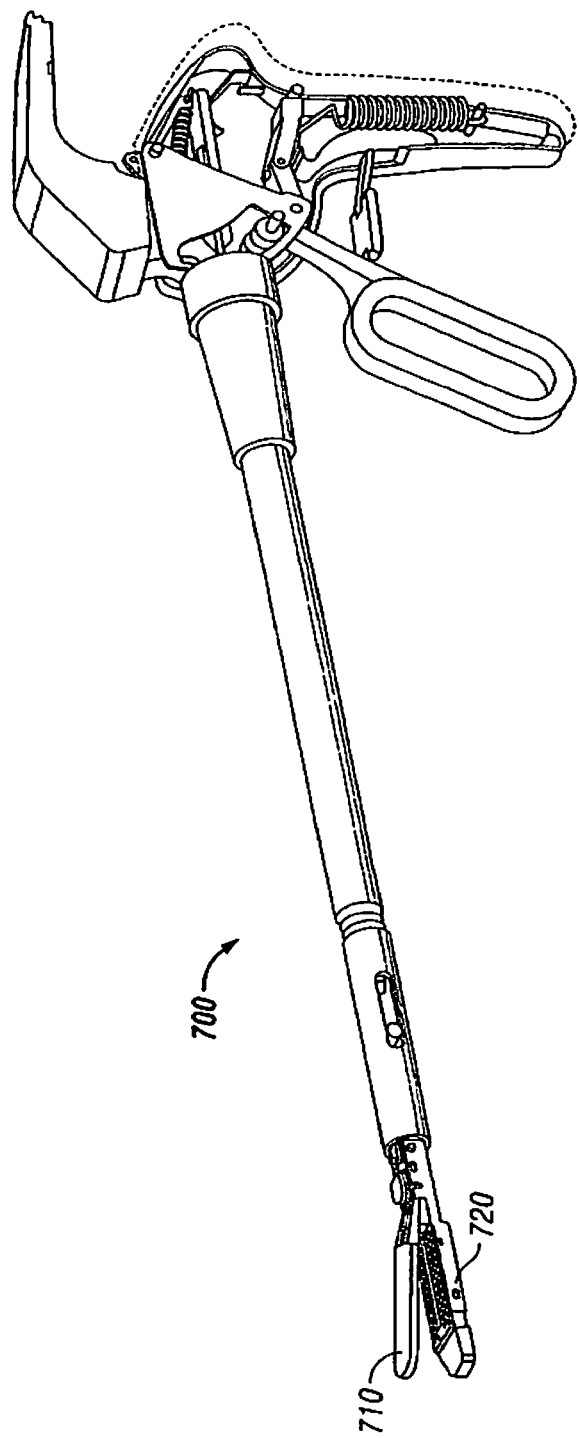
FIG. 7 is a perspective view of a surgical stapler having a staple cartridge in accordance with an embodiment of the present disclosure.

The present disclosure also relates to a surgical staple, such as those described above, for use with a surgical stapler such as endoscopic surgical stapler 700 by way of example, shown in FIG. 7. Surgical stapler 700 includes a staple cartridge 720 and anvil portion 710, including a plurality of pockets. Anvil portion 710 is spaced apart from cartridge portion 720 such that staple cartridge 720 and anvil portion 710 are configured to compress tissue "t" therebetween. The present disclosure further relates to staple cartridge 720 for use with surgical stapler 700. Staple cartridge 720 includes a plurality of surgical staples, such as those described above, in a spaced relation to each other. While a particular type of surgical stapler 700 is illustrated in FIG. 7, a staple cartridge of the present disclosure containing the staples disclosed herein, preferably in linear or annular rows, may be used in connection with any suitable surgical stapler, including for example open staplers and endoscopic staplers and circular or linear staplers.

While the above description and accompanying figures illustrate the cross-sections of surgical staples of the disclosed embodiments having a particular length and height, it is envisioned that surgical staples having different cross-sections may also be utilized in connection with the disclosed channel, channels or rib. For example, the present disclosure incorporates surgical staples having at least one channel or rib extending substantially continuously through at least the leg members and having cross-sections where the length dimension is greater than the height dimension. The inclusion of at least one channel or rib will further reduce the amount of force required to properly form a staple and/or help bias the staple leg members to form in a desired orientation.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended hereto.

The invention claimed is:

1. A surgical staple comprising:
   a linear backspan;
   first and second leg members extending from the linear backspan, each leg member of the first and second leg members including an inner surface and an outer surface diametrically opposing the inner surface, the inner surface of the first leg member facing the inner surface of the second leg member; and
   at least one channel extending along at least one of an inner surface and an outer surface of the linear backspan and at least one of the corresponding inner surface and outer surface of the first and second leg members, the at least one channel being open along the entire length thereof, wherein each leg member of the first and second leg members includes a tissue penetrating portion including an angled surface configured to facilitate penetration thereof through tissue.

2. The surgical staple according to claim 1, wherein the at least one channel is semi-circular.

3. The surgical staple according to claim 1, wherein at least one of the first or second leg members includes a substantially uniform transverse cross-section along its length.

4. The surgical staple according to claim 1, wherein a width of the at least one channel is between about 0.004 inches and about 0.007 inches.

5. The surgical staple according to claim 1, wherein a depth of the at least one channel is between about 0.001 inches and about 0.004 inches.

6. The surgical staple according to claim 1, wherein the surgical staple is formed from a material selected from the group consisting of titanium and stainless steel.

7. A staple cartridge supported on a surgical stapler, the staple cartridge comprising:
   a plurality of surgical staples in a spaced relation to each other, each surgical staple of the plurality of surgical staples including:
   a planar backspan;
   a pair of deformable legs extending from the planar backspan, the pair of deformable legs configured to come into contact with anvil pockets of the surgical stapler for formation of a B-shaped surgical staple; and
   at least one open channel extending along at least one of an inner surface and an outer surface of each deformable leg and a corresponding surface of the planar backspan, wherein each leg of the pair of deformable legs includes a tissue penetrating portion having an angled surface configured to facilitate insertion through tissue.

8. The staple cartridge according to claim 7, wherein the at least one open channel is semi-circular.

9. A surgical staple comprising:
a backspan defining a plane;
first and second leg members extending from the backspan, the first and second leg members each including a first surface and a second surface diametrically opposing the first surface, the first surface of the first leg member facing the first surface of the second leg member, each leg member of the first and second leg members including an angled tissue penetrating portion configured to facilitate penetration through tissue;
a channel extending along the backspan and the first and second leg members, the channel being open along the entire length thereof; and
a rib extending along the backspan and the first and second leg members, the rib diametrically opposing the channel.

10. The surgical staple according to claim 9, wherein a transverse cross-section of each leg member of the first and second leg members includes a length and a height, the height defined by a distance between a wall defining the channel and an opposing wall including the rib, and the length being greater than the height.

11. The surgical staple according to claim 9, wherein the first and second leg members are substantially orthogonal to the plane of the backspan.

12. A surgical staple comprising:
a backspan defining a plane;
first and second leg members extending from the backspan, the first and second leg members each including a first surface and a second surface diametrically opposing the first surface, the first surface of the first leg member facing the first surface of the second leg member, the first and second leg members substantially orthogonal to the plane of the backspan;
a channel extending along the backspan and the first and second leg members, the channel being open along the entire length thereof; and
a rib extending along the backspan and the first and second leg members, the rib diametrically opposing the channel.

13. The surgical staple according to claim 12, wherein each leg member of the first and second leg members includes an angled tissue penetrating portion configured to facilitate penetration through tissue.

* * * * *